United States Patent [19]

Herman et al.

[11] Patent Number: 4,850,351

[45] Date of Patent: Jul. 25, 1989

[54] WIRE GUIDED LASER CATHETER

[75] Inventors: Stephen J. Herman, Andover, Mass.;
Laurence A. Roth, Hudson, N.H.;
Edward L. Sinofsky, Reading, Mass.;
Douglas W. Dickinson, Jr.,
Merrimack, N.H.

[73] Assignee: C. R. Bard, Inc., Murray Hill, N.J.

[21] Appl. No.: 934,629

[22] Filed: Nov. 25, 1986

Related U.S. Application Data

[63] Continuation-in-part of Ser. No. 736,804, May 22, 1985, abandoned.

[51] Int. Cl.$^4$ ............................................. A61B 17/36
[52] U.S. Cl. ...................... 128/303.1; 128/4; 128/348.1; 604/21; 138/121
[58] Field of Search ............... 604/21, 20, 280; 128/6, 128/4, 303.1, 634, 633, 348.1; 138/120, 121

[56] References Cited

U.S. PATENT DOCUMENTS

| | | | |
|---|---|---|---|
| 2,498,692 | 2/1950 | Mains | 128/348 |
| 3,572,325 | 3/1971 | Bazell | 128/6 |
| 3,674,014 | 7/1972 | Tillander | 604/95 |
| 3,788,304 | 1/1974 | Takahashi | 128/6 |
| 3,799,151 | 3/1974 | Fukaumi | 128/4 |
| 4,175,545 | 11/1979 | Termanini | 604/21 X |
| 4,211,229 | 7/1980 | Wurster | 128/303.1 |
| 4,273,109 | 6/1981 | Enderby | 128/6 |
| 4,290,421 | 9/1981 | Siegmund | 128/6 |
| 4,341,205 | 7/1982 | Hosono | 128/6 |
| 4,427,000 | 1/1984 | Ueda | 128/6 |
| 4,469,098 | 9/1984 | Davi | 128/303.1 |
| 4,540,404 | 9/1985 | Wolvek | 604/96 |
| 4,545,390 | 10/1985 | Leary | 128/772 |
| 4,648,892 | 3/1987 | Kittrell et al. | 128/303.1 X |
| 4,681,104 | 7/1987 | Edelman | 128/303.1 |

FOREIGN PATENT DOCUMENTS

| | | |
|---|---|---|
| 0031073 | 1/1981 | European Pat. Off. |
| 2820239 | 11/1978 | Fed. Rep. of Germany |
| 2950792 | 7/1980 | Fed. Rep. of Germany |
| 2368256 | 6/1978 | France |

Primary Examiner—Stephen C. Pellegrino
Attorney, Agent, or Firm—Wolf, Greenfield & Sacks

[57] ABSTRACT

A catheter having optical fibers for delivering laser energy to a blood vessel to remove obstructions in the blood vessel is adapted to be guided controllably and selectively by a guide wire to the site to be treated. The catheter includes a central lumen which is open at the distal end of the catheter and which receives the guide wire so that the catheter may be advanced over the guide wire. A relatively few number of optical fibers are contained within and extend longitudinally of the catheter wall. The distal tip of the catheter is provided with a cylindrical optically transparent end cap and means are provided to securely mount the distal ends of the optical fibers with respect to the end cap so that the light emitted from the ends of the fibers passes through the cylindrical wall of the end cap and is emitted at the distal emissions face of the end cap. The catheter embodies a special construction of an inner catheter core and a surrounding sheath which provides for a high degree of flexibility to enable the catheter to be passed through tortuous passages in a patient's vasculature. The inner core is formed from a plurality of articulated segments and is surrounded by a thin flexible sheath. Longitudinal flutes formed along the articulated segments of the core receive and retain the optical fibers in a manner which permits the fibers, sheath and core to shift longitudinally with respect to each other to provide a very high degree of flexibility for the composition catheter.

39 Claims, 4 Drawing Sheets

WIRE GUIDED LASER CATHETER

This application is a continuation-in-part of application Ser. No. 736,804, filed May 22, 1985 now abandoned and entitled WIRE GUIDED LASER CATHETER.

FIELD OF THE INVENTION

This invention relates to catheters and techniques for delivering and applying laser energy to a location within the human body.

BACKGROUND OF THE INVENTION

Although the theoretical possibilities for the medical use of laser energy have been recognized for a long time, its practical use has been limited to only a few types of procedures. Typically, the procedures in which laser energy has been used for treatment have been in readily exposed, easily accessible portions of the body, such as the patient's skin and eyes. While it has been suggested for some time that laser energy might be useful in the recanalization of obstructed blood vessels to remove the obstruction from the blood vessel, a satisfactory, practical system has not yet been developed. A major obstacle in the development of techniques for applying laser energy to blood vessels has been in the problem of how to deliver the laser beam precisely to the vascular site to be treated and then, how to apply controllably the laser beam so as to remove the biological material causing the blockage without damaging or otherwise adversely affecting the patient's vasculature. The difficulties presented have been compounded further by the dimensional limitations which must be imposed on any catheter which is to be inserted into a blood vessel, particularly narrow blood vessels such as coronary arteries which may have lumens of the order of 1.5 to 4.5 millimeters in diameter.

Among the difficulties is the manner of placing and locating the distal end of the catheter so that it is positioned properly with respect to the obstruction. Prior proposals, which have included the use of supplemental optical fibers to transmit illuminating light into the blood vessel in conjunction with other groups of fibers to permit visual observation of the interior of the blood vessel, are not practical because they are too large and too stiff for use in narrow arteries. Another difficulty which has been presented is that there often may be materials such as blood, in the region between the emission point of the laser beam at the end of the fiber and the obstruction. Such material may obstruct the optical path. The blood may become charred at the distal emitting tip of the fiber which can result in overheating and destruction of the optical fiber. Still another difficulty is that such a catheter which is to be advanced to small, distally located arteries must be very flexible to be able to make sharp, short radius bends in order to reach those arteries. The catheter also must have a small diameter, yet must be capable of being pushed and manipulated, from its proximal end, without becoming bunched up or bent as it advances within the patients blood vessels. A further, very desirable feature of such a catheter is that it should be capable of providing fluid communication from the proximal to the distal end of the catheter, to enable liquid infusion or to make pressure measurements. The development of a practical catheter which achieves the foregoing objects while avoiding the above and other difficulties has proved to be a substantial problem.

Although many laser catheters have been proposed in the past, none has proved to be usable to any practical degree. All suffer from one or more of various difficulties. It is among the general objects of the invention to provide a practical and effective catheter system by which laser energy can be delivered to selected sites in a patient's blood vessels with precision and control.

SUMMARY OF THE INVENTION

The catheter is capable of and is intended to be used with a guide wire. A central lumen, which receives the guide wire, extends fully through the catheter and is open at the distal end of the catheter. The catheter has a very small outer diameter, of the order of 1.5 millimeters, and is small enough to be advanced deeply into the patient's more narrow blood vessels.

A plurality of optical fibers are contained within the wall of the catheter. The distal end of the catheter includes an optically transparent cylindrical cap which covers and protects the distal ends of the optical fibers. The cap has a central aperture which defines the distal outlet aperture of the lumen with the distal end of the cap defining an annular, ring-like configuration about the aperture. The distal ends of the optical fibers are mounted securely with respect to the end cap so that light emitted from the fibers passes through the distal annular portion of the cap and is emitted from the ring-shaped distal end face of the cap.

The proximal end of the catheter includes a branch fitting from which extends a plurality of tubes, there being one tube to receive the proximal end of each optical fiber. The proximal end of the each tube has a connector by which the optical fibers may be connected individually to a laser light source. Each of the optical fibers is independent of the other and each can be used and controlled independently of the others should that be desired.

Another tube extending from the proximal fitting at the proximal end of the catheter is in communication with the proximal end of the central lumen of the catheter and provides access for a guide wire. The guide wire may be a very small diameter, steerable guide wire, such as that described in U.S. patent application Ser. No. 421,315 filed Sept. 22, 1982, now U.S. Pat. No. 4,545,390, issued Oct. 8, 1985. The cross sectional dimensions and shape of the guide wire and the catheter lumen are such that when the guide wire is in place, adequate flow area will remain within the lumen to permit pressure measurements to be taken in the blood vessel beyond the distal end of the catheter and also to permit liquids to flow through the lumen.

In another aspect of the invention the catheter is constructed as to be highly flexible so as to be adapted to follow relatively short radius, sharply curved paths along the patient's vasculature. The catheter includes a composite wall construction which includes an inner core, through which the central lumen is formed, and an outer sheath. The sheath is not secured to the core and is permitted to slide and shift longitudinally with respect to the core when the catheter is bent. The core is formed to include a plurality of flutes which extend longitudinally along the outer surface of the core. The flutes receive the individual optical fibers. The fibers are retained within the flutes by the surrounding sheath which, although not secured to the core, is dimensioned to cover the flutes and prevent the fibers from shifting out of their respective flutes. The fibers are freely shiftable longitudinally within the flutes. When the catheter is bent, all of the longitudinally extending components are free to shift to minimize resistance to bending. In addition, the flexibility of the composite catheter is enhanced further by forming the core in an articulated configuration. The core is formed to include reduced diameter peripheral notches at spaced locations along the core shaft. The notched sections are more flexible and enable the catheter to be bent to very small radius curves. The flexibility of the catheter may be varied along its length by varying the longitudinal spacing of the notches.

It is among the objects of the invention to provide a small diameter guidable laser catheter which is highly flexible and maneuverable.

Also among the objects of the invention is to provide a laser catheter which can be placed with the use of a guide wire.

Another object of the invention is to provide a laser catheter having a central lumen adapted to receive a guide wire and in which the lumen provides fluid communication from the proximal to the distal end of the catheter to permit pressure measurement and liquid flow while the guide wire is in place in the lumen.

A further object of the invention is to provide a laser catheter of the type described in which the tip of the fibers are isolated to protect the fiber.

Another object of the invention is to provide a laser catheter having a plurality of optical fibers extending through the catheter, for delivery of laser energy, in which the individual fibers are provided with separate connective fittings and in which the transmission of energy through the fibers is controllable independently of the others.

A further object of the invention is to provide a catheter of the type described in which the objects of the invention are achieved within the context of a small outer diameter catheter, of the order of 1.5 millimeters diameter.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
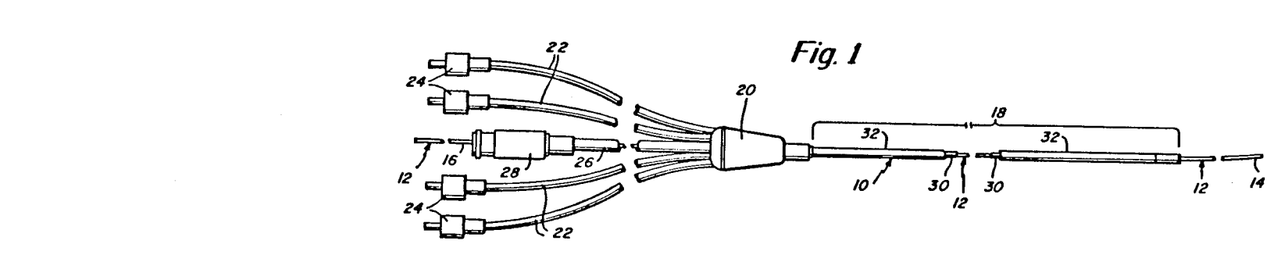
FIG. 1 is a fragmented illustration of the catheter having a guide wire extending therethrough.

FIG. 1 illustrates the catheter, indicated generally by the reference character 10, with a guide wire, indicated generally at 12, extending through the catheter. The guide wire 12 is shown with its distal end 14 projecting out of the distal end of the catheter 10 and with its proximal end 16 extending out of and being exposed at the proximal end of the catheter 10. The catheter 10 has an elongate main portion 18 which, by way of example only, may be of the order of 160 centimeters long. The guide wire may be of the order of 180 centimeters long, or more. As will be described in further detail, the invention enables the catheter to have a main portion 18 with an outer diameter of the order of 1.5 millimeters. A branch fitting 20 is molded securely to the proximal end of the main portion 18 of the catheter 10 and a plurality of tubes 22 extend proximally from the fitting 20. The tubes 22 are intended to carry optical fibers, described below, each tube 22 being provided with a single fiber and having a connector 24 at its proximal end by which the fiber within each of the tubes 22 may be connected to a source of laser light.

The catheter 10 includes an additional flexible tube 26 extending proximally from the fitting 20 which communicates with a lumen extending through the catheter through which the guide wire 12 may be passed. The tube 26 has a fitting 28 on its proximal end. Fitting 28 may be a Luer-Lok fitting to enable the tube 26 to be easily and quickly connected to liquid infusion devices and/or pressure monitoring devices. The fitting 28 can be connected to a conventional Y-fitting to permit the guide wire 12 to be controlled while also permitting liquid infusion and pressure monitoring.

The main portion 18 of the catheter 10 includes an inner elongate core 30 which is surrounded by an outer elongate sheath 32. As shown in further detail in FIGS. 2-5 the inner core 30 has a lumen 34 which extends centrally along and within the core 30. The lumen 34 may be circular in cross section although in the preferred embodiment a non-circular cross section is preferred, such as the four-lobed shape shown in FIG. 5 having alternate lands 36 and groove-like lobes 38. The lobes 38 cooperate with the guide wire 12 which has a circular cross section (illustrated in phantom in FIG. 12) to define an enlarged cross sectional flow area in the space between the guide wire 12 and the inner, lumen-defining surface of the core 34. The guide wire 12 and core lumen 34 are arranged to provide a clearance within the lumen 34 to permit liquid to flow and pressure measurements to be made through the lumen 34 while the guide wire 12 is in place in the lumen. The proximal tube 26 is connected within the fitting 20 to the core 30 so that the lumen 34 is in communication with the lumen of the tube 26.

Figure 2:
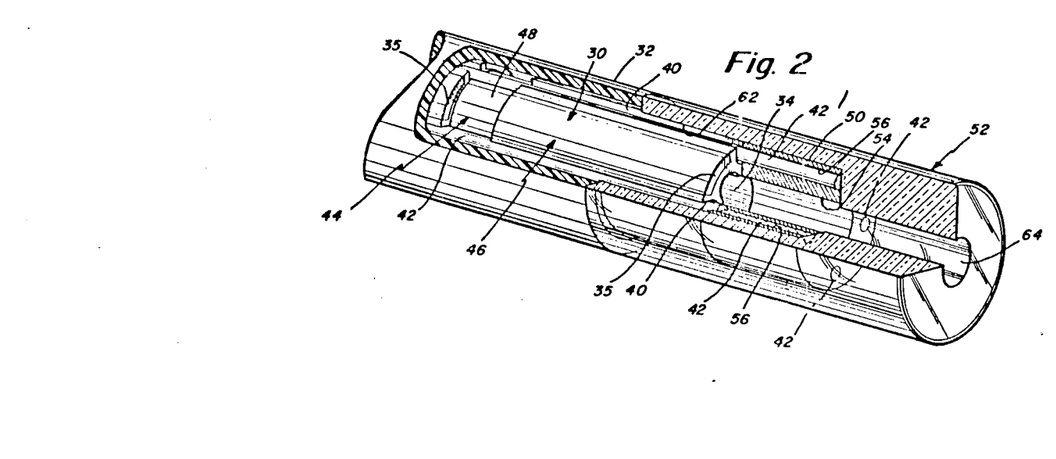
FIG. 2 is an isometric illustration of the distal portion of the catheter, broken away and shown in quarter section (enlarged)
Figures 3, 4, 5, 6:
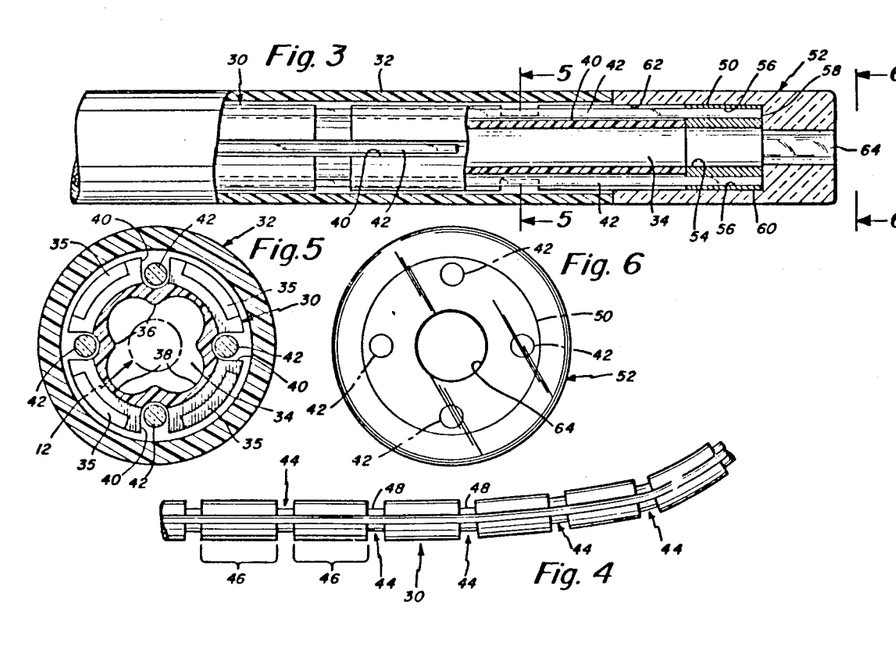
FIG. 3 is a longitudinal section of the distal region of the catheter.
FIG. 4 is a longitudinal illustration of a section of the main core shaft with the catheter sheath removed to illustrate the articulated nature of the core shaft.
FIG. 5 is an enlarged cross-sectional illustration of the catheter as seen along the line 5—5 of FIG. 3 with the position of the guide wire within the lumen illustrated in phantom.
FIG. 6 is an end view of the distal end of the catheter as seen along the line 6—6 of FIG. 3.

The core 30 also is provided with a plurality of longitudinally extending circumferentially spaced flutes 40. Each of the flutes 40 receives waveguide means, such as an optical fiber 42 adapted to transmit radiant energy, such as laser light. The optical fibers 42 are not secured within the flutes 40 and are permitted to shift longitudinally within the flutes as the catheter is bent. The distal ends of the fibers 42 are secured within the distal portion of the catheter, in a manner which will be described. The proximal ends of the fibers 42 pass through the fitting 20, extend through the flexible tubes 22 and are secured at their proximal ends within the optical connectors 24. The tubes 22 are secured within the fitting 20 and the fitting is formed to provide a smooth transition and passage for the fibers 42 from the flutes 40 through the fitting 20 into the tubes 22.

The outer sheath 32 covers the core 30 and fibers 42 and serves to retain the fibers 42 within the flutes 40. Except for its connections to the catheter at its proximal and distal ends, the sheath 32 also is not attached to the core 30 or to the optical fibers 42. Thus, there are no points of attachment along the length of the catheter between the core 30, optical fibers 42 or sheath 32 which enhances the high degree of flexibility of the catheter by minimizing internal resistance to bending of the catheter.

The sheath 32 preferably is formed from a heat shrinkable material, such as PTFE, and is heat shrunk about the core 32, but not to a degree of tightness which would impair the freedom of the sheath and core to shift with respect to each other when the catheter is bent. By way of example, the core may have a diameter of the order of 0.046" and the sheath may have an inner diameter of about 0.050" and a wall thickness of about 0.003", thus leaving a very slight clearance between the core and sheath.

The flexibility of the catheter is enhanced further by forming the core 30 so that it defines a series of articulated segments. FIG. 4 illustrates a portion of the core from which it may be seen that the core is provided with a plurality of longitudinally spaced, circumferential notches 44. The notches separate and define the core into a plurality of serially arranged core segments 46 connected by smaller diameter and shorter connective segments 48. The arrangement of articulated core segments 46 increases the flexibility of the core 30 and, therefore, increases the flexibility of the composite catheter. The connective segments 48 are smaller in diameter and present less resistance to bending so that a bending force applied to the catheter will cause the core to bend at the connective segments 48. The connective segments 48 may be spaced in equal distances along the length of the catheter to provide a uniform degree of flexibility for the catheter along its length. However, if it is desired to vary the flexibility of the catheter, at any location, that may be achieved by varying the spacing of the connective segments 48. By spacing the segments 48 closer to each other, the resulting catheter segment will have a higher degree of flexibility than where the spacing is greater and in where the length of the core segments 46 is larger. For example, it may be desirable to provide a catheter in which the distal region is more flexible than the proximal portions so as to permit the distal region to be bent into sharper radius curves. Variations in the flexibility of the catheter also may be achieved by varying the length of the connective segments 48 as well as the core segments 46. By way of example, in a catheter having the dimensions described above the core segments 46 may be between about one to four millimeters long and the connective segments may be one-half to one millimeter in length.

The core 30 preferably is formed from a material having a relatively low coefficient of friction, such as PTFE, to reduce resistance of the guide wire within the lumen 34. The guide wire preferably is also coated with a low friction material such as PTFE to further reduce friction between the two.

The core 30 preferably is provided with radiopaque stripes 35 which extend lengthwise of the core. The stripes 35 may be formed by radiopaque materials added to the resin from which the core is extruded according to procedures well known in the art. In the preferred embodiment a plurality of radiopaque stripes 35 are formed between adjacent flutes 40. The radiopaque stripes 35 preferably are formed only on the outer surface of the core so that the inner surface may remain defined completely by the low friction material. It may be noted that the radiopaque stripes are interrupted at the notches 44. The resulting stripe, however, presents a sufficiently continuous radiopaque image as to be effective in visualizing its position under fluoroscopy.

The distal ends of the optical fibers 42 are secured together by a fiber holder 50 which is secured to the fibers 40 at their distal ends. The fiber holder 50 is contained within and also is secured to an optically transparent distal cap 52 which is formed from an optical glass or crystalline equivalent which is transmissive to the wavelength of radiant energy with which the catheter is to be used. The cap serves to isolate the fibers 40 from the vascular environment and protects them from exposure to biological material.

The fiber holder 50, shown also in FIG. 6, preferably is formed from a radiopaque material, such as stainless steel or a more radiopaque material such as platinum or silver. The fiber holder 50 is cylindrical and is provided with a central aperture 54 which preferably is substantially about the same size as the lumen 34 in the core 30. The central aperture 54 may be circular or lobe shaped, although a circular aperture 54 may be used in a catheter in which the central lumen 34 is lobe shaped as shown in FIG. 5. The fiber holder 50 is provided with a plurality of longitudinally extending holes 56 which extend through the wall of the holder 50 and receive, in a snug fit, the distal ends of the optical fibers 40. The distal face 58 of the combined fibers 40 and fiber holder 50 is polished flat to butt flush against an annular shoulder 60 formed in the optically transparent cap 52.

The cap 52 is cylindrical and has the same outer diameter as the sheath 32 so that they may define a smooth and continuous consistent outer diameter. The cap 52 has an enlarged bore 62 formed in its proximal end. The bore terminates at and defines the internal shoulder 60 and a smaller diameter central aperture 64 is formed in the distal end of the cap 52. The central aperture 64 may be the same diameter as the aperture 54 in the fiber holder 50 to provide a smooth and continuous passage which opens at the distal tip of the catheter. However, the central aperture 64 may be somewhat narrower than the lumen 34 as long as sufficient clearance is provided about the guide wire so as not to adversely interfere with fluid flow and pressure measurement. Some restriction in the flow area can be tolerated at the distal tip as long as the restriction extends over a relatively short length, as would be the case if the openings 64 and 54 presented somewhat of a narrowed or partly restricted flow area.

The cap 52 is secured, as by an epoxy adhesive, principally to that portion of the core 30 and the fibers 42 which are disposed within the proximal end of the cap 52 and also may be secured to the fiber holder 50. The distal end of the sheath 32 is simply butted against the proximal end of the cap 52 and need not be adhesively connected to the cap 52.

By way of example the cap 52 may be formed from a pair of Pyrex brand glass cylinders which are fusable to each other. Thus, the cap 50 may be formed from an elongate relatively large diameter Pyrex glass sleeve and a relatively short, smaller diameter Pyrex glass sleeve, the smaller sleeve fitting within and being fused to one end of the outer sleeve. The end where the two sleeves are joined defines the relatively thick walled distal segment 72 (see FIG. 7). The faces 60, 74 may be polished so as to be optically flat. Alternatively, the smaller diameter sleeve may be formed from artificial sapphire, transparent to laser light, plugged into the end of the larger Pyrex sleeve. The distal face of the sapphire plug may be chamfered about its periphery. The Pyrex sleeve may be heated to cause its distal end to flow over the chamfer to lock the sapphire in place. The foregoing arrangement serves to position securely the distal ends of the fibers 42 and in a manner which protects and isolates the fibers 42 from exposure to and contact with biological material.

Figure 8:
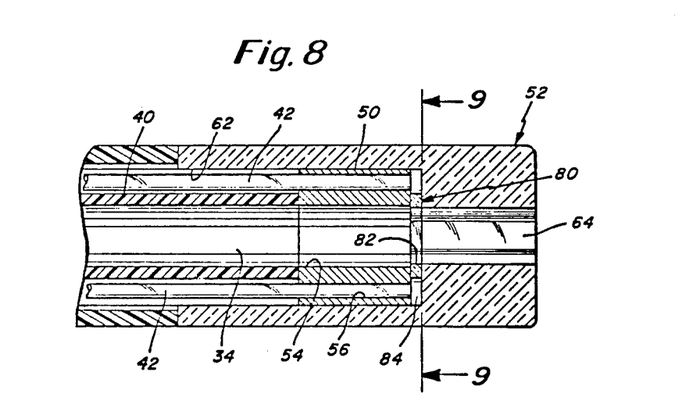
FIG. 8 is a longitudinal section of the cap region of a modified embodiment of the catheter.
Figure 9:
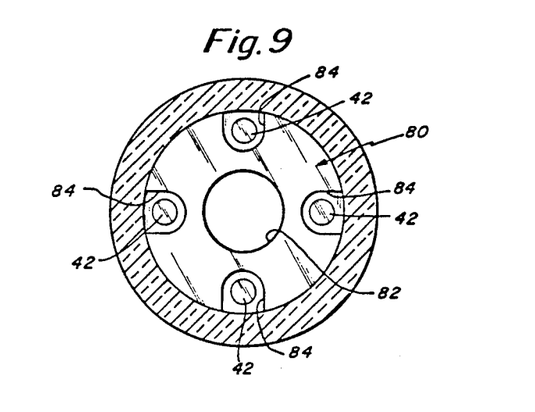
FIG. 9 is a sectional illustration of the catheter as seen along the line 9—9 of FIG. 8.

FIGS. 8 and 9 illustrate a modification to the distal end of the catheter which provides an enhanced seal to protect completely and isolate the fibers 42 from exposure to water or biological material. In this embodiment, a gasket 80 is interposed between the distal face of the holder 50 and proximal face 60 of the cap 52. The gasket 80 is formed from a thin sheet of optically transparent biocompatible material such as medical grade Silastic silicone rubber which is commercially available from the Dow Corning Company. By way of example, the gasket may be of the order of 0.005"-0.008" thick. The gasket 80 has a central opening 82 which is of the same diameter as the opening 64 in the distal end of the cap 52. The outer diameter of the gasket 80 is arranged to fit closely within the enlarged bore 62 of the cap 52. The gasket 80 is provided with cut-outs 84 about its periphery located in alignment with the optical fibers 42 to permit the laser energy to pass from the fiber 42 to the cap 52 without passing through the gasket. Although the gasket preferably is as near as optically transparent as possible so as to permit reflection of radiated energy or re-reflection of reflected light (as will be described), it may not, as a practical matter, be sufficiently optically transparent to the direct laser energy emitted from the end of the optical fiber. Slight imperfections in the gasket or dust particles on the gasket, if in the path of the laser beam, would absorb energy and cause overheating and possible destruction of the distal end of the catheter. The cut-outs 84 take the gasket out of the way of the laser beams while enabling the gasket arrangement to enhance the seal between the holder 50 and cap 52 and prevent any fluid or other contaminant material from reaching the distal end of the fiber 42.

In order to maximize the flexibility of the catheter it is preferred to use relatively few optical fibers. The beam pattern emitted by the catheter preferably should diverge to define a diameter slightly beyond the end of the catheter which is just slightly greater than the diameter of the catheter so that the hole formed through the biological material by the laser energy will be large enough to permit the catheter to be passed through it. Moreover, it is preferred to accomplish that with a relatively few number of optical fibers so as not to impair the high degree of catheter flexibility which is preferred. A catheter having a very small diameter, of the order of 1.5 millimeters can achieve these objectives using an arrangement of four optical fibers equiangularly spaced about the central axis of the catheter. It should be understood, however, that the advantages of the invention can be achieved using somewhat more, or possibly even fewer than four optical fibers, although it is preferred to maintain the number at the minimum required in order to form the desired beam pattern.

Figure 7:
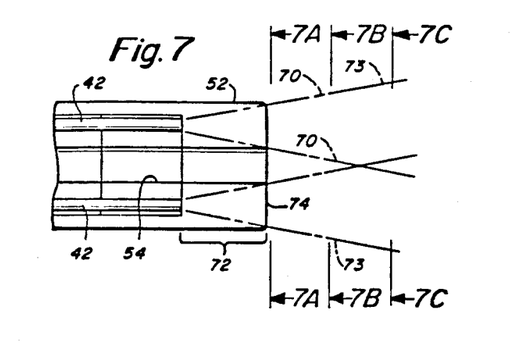
FIG. 7 is a diagrammatic side view of the distal tip of the catheter illustrating the pattern of light rays emitted from the distal end of the catheter.
Figure 7A:
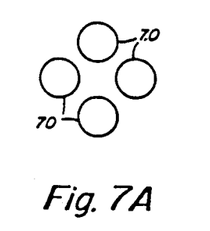
FIGS. 7A, 7B and 7C are diagrammatic illustrations of the beams emitted from the catheter having four optical fibers as seen along the image planes indicated at 7A—7A, 7B—7B and 7C—7C of FIG. 7.
Figure 7B:
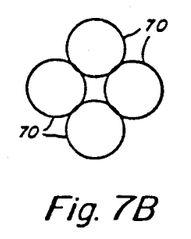
Figure 7C:
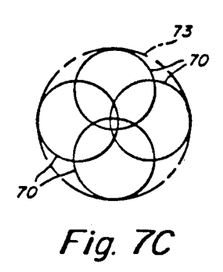

FIG. 7 illustrates, diagrammatically, the beam pattern of a pair of diametrally opposed fibers. The beam as defined by $1/e_2$ radius is suggested by the ray lines 70 in FIG. 7. The beam from each individual fiber 42 is emitted from the distal face of the fiber 42 and enters the distal segment 72 of the cap 52 through the face defining the shoulder 60. The beam is divergent and, in the illustrative embodiment, may have a half angle of the order of between about 6° to 16°, depending on the numerical aperture of the fiber. The diverging beam from each of the fibers 42 exits from the distal emission face 74 at the end of the cap 52. FIGS. 7A, 7B and 7C illustrate the beam pattern, in cross section, as seen along the image planes 7A, 7B and 7C in FIG. 7. At the emission face 74 of the cap 52 the beams, in the illustrative embodiment, are still separate. At the plane 7B—7B the beams have further diverged and have begun to overlap. At the plane indicated at 7C—7C the beams have overlapped and define an envelope 73 having an outer diameter which is slightly greater than the diameter of the catheter. Preferably the beams 70 have overlapped to merge and fill in a continuous pattern within a distance from the distal face 74 which is approximately equal to the outer diameter of the catheter, about 1.5 millimeters in the illustrative embodiment. The length of the distal segment 72 preferably is determined so that the distance between the distal face 74 of the cap 52 and the substantially filled-in image plane is as desired.

In another aspect of the invention the optics at the distal end of the catheter are arranged to minimize reflection. In that regard it should be understood that some of the light emitted from the catheter may be reflected by the biological material within the blood vessel. Additionally, light in the infrared portion of the spectrum may be radiated from biological material which is heated by the absorption of radiant energy. Reflection is undesirable because the reflected light and emitted IR radiation may be absorbed by the components at the distal end, such as the fiber holder 50 and epoxy which joins the fibers to the holder, and may cause them to overheat and possibly be destroyed. In order to protect the device from reflection and from emitted IR radiation the distal face 58 of the fiber holder 50 and the distal ends of the fibers 42 are highly polished to provide a reflective surface. Additionally, the epoxy used preferably is reflective and, for example, may be silver filled. Light which is reflected or emitted from the biological tissue back toward the catheter will be re-reflected by the face 58 and thereby returned toward the biological material. Additionally, it is preferred to provide an anti-reflection coating on the proximally facing shoulder surface 60 of the cap to maximize transmission of light distally through the surface 60. To the extent that some reflected or emitted radiation may be absorbed, the heat is absorbed by the metal fiber holder 52 which serves to dissipate the heat so as to further avoid the risk of building up dangerous heat levels.

The catheter may be used in a number of protocols depending on the preference of the physician and the vascular anatomy to be treated. For example, the catheter 10 may be preassembled with the guide wire 12 extending through the catheter, with the distal tip of the guide wire retracted in the distal end of the catheter. The combined catheter and guide wire then may be advanced together through a previously placed guide catheter which will have been placed so that its distal tip will be at the entry to a coronary artery to be treated. The distal end of the combined catheter and guide wire then may be advanced slightly into the coronary artery and then the guide wire may be advanced, alone, through the artery. The guide wire 12 may be manipulated to advance selectively into the arterial branch where the stenosis to be treated is located. Once the guide wire has been placed, the catheter can be advanced over the guide wire and will follow the guide wire to bring the distal end of the catheter to the intended site. The positioning of the guide wire and the catheter may be monitored fluoroscopically. Additionally radiopaque dye may be injected through the catheter lumen 34 at any time during the procedure when it is desired to visualize fluoroscopically the coronary anatomy.

Liquids, such as radiopaque dye, may be injected at any time even while the guide wire is in place. Flushing liquids, such as saline also can be delivered and liquid and debris can be aspirated through the catheter. Similarly, arterial pressure measurements may be taken at any time even while the guide wire is in place. The catheter is advanceable easily over the guide wire and is highly flexible so as to be capable of following any curve or bend in the guide wire necessary to follow the contour of the patient's vasculature. Once the catheter has been advanced to the desired location laser energy may be applied through the optical fibers and delivered to the site to be treated. The laser energy may be applied simultaneously through all of the optical fibers 42 or it may be applied selectively through the individual fibers.

Thus, the invention provides a catheter and system for delivering laser energy to remote and difficult to reach regions of a patient's vasculature. The invention enables a laser catheter to be placed with the aid of a guide wire and is constructed to be highly flexible so as to be capable of making sharp, small radius bends. The system enables pressure measurement and liquid infusion without requiring withdrawal of the guide wire. Moreover, these and other advantages are achieved within a very small diameter catheter.

It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

1. A catheter for removing biological material by laser energy, the catheter having a proximal end and a distal end and comprising:
    means defining a lumen extending through the catheter, the lumen being open at the distal end of the catheter, said means including a catheter wall;
    means at the proximal end of the lumen for permitting fluid communication with the lumen and to permit a guide wire to be received within the lumen;
    a plurality of flexible optical conductors extending longitudinally of the catheter and within the catheter wall;
    a distal cap mounted on the distal end of the catheter and covering the distal end of the fibers, the distal cap having a distal surface defining an emission surface and providing an optical path from the distal end of the fibers to the emission surface;
    an aperture formed through the distal cap in communication with the catheter lumen;
    the flexible optical conductors being unattached to the catheter except at the ends of the conductor;
    the catheter wall being defined by an elongate core having said lumen extending therethrough and a flexible sheath surrounding the core;
    a plurality of flutes formed longitudinally along he outside of the core, the conductors being received in and extending along the flutes and being retained in the flutes by the sheath;
    said conductors, core and sheath being substantially unattached to each other along their lengths thereby to enable the core, conductors and sheath to shift longitudinally with respect to each other thereby to permit their simultaneous bending but without any of said core, conductor or sheath restricting the bending of the others.

2. A catheter as defined in claim 1 further comprising means for connecting the conductors securely with respect to the core at the distal end of the core.

3. A catheter as defined in claim 2 further comprising:
    the proximal end of the catheter having a plurality of optical connectors, each associated with a conductor thereby to enable independent control of the optical conductors.

4. A catheter as defined in claim 2 further comprising:
    said conductors being secured by a holder ring having a central aperture and a plurality of circumferentially spaced apertures in the ring, each of the circumferentially spaced apertures receiving the distal end of a conductor,
    said holder ring being secured to the cap.

5. A catheter as defined in claim 4 wherein the holder ring is radiopaque.

6. A catheter as defined in claim 4 wherein the distal cap comprises:
    a cylindrical member having a proximal bore adapted to receive the holder ring and the distal end of the core,
    the cap having a smaller aperture formed distally of and in communication with the proximal bore, the smaller aperture opening at the distal end of the cap;
    the juncture of the bore and aperture defining a shoulder;
    the distal face of the holder being in engagement with the shoulder.

7. A catheter as defined in claim 6 wherein the distal end of the sheath butts against the proximal end of the cap and is of substantially the same diameters the cap.

8. A catheter as defined in claim 4 further comprising:
    the distal face of the holder and the conductors secured thereto being flush and being highly polished to define a highly reflective surface adapted to reflect light which is directed proximally from the biological material thereby to minimize absorption of the reflected light by the holder.

9. A catheter as defined in claim 8 wherein said proximally directed light comprises one or both of reflected laser light or infrared radiation emitted by the biological material.

10. A catheter as define in claim 4 wherein the distal cap comprises:

a cylindrical member having a proximal bore adapted to receive the holder ring and a distal end of the core, the cap having a small aperture formed distally of and in communication with the proximal bore, the smaller aperture opening at the distal end of the cap;

the juncture of the bore and aperture defining a shoulder;

the gasket in engagement with the shoulder;

the distal face of the holder being in engagement with the proximal face of the gasket and cooperating with the cap to secure the gasket therebetween;

the gasket having a central opening in registry with the smaller aperture of the cap and having cut-out portions in alignment with the conductor means.

11. A catheter as defined in claim 10 wherein the gasket is optically transparent.

12. A catheter as defined in claim 10 further comprising:

the distal face of the holder and the conductors secured thereto being flush and being highly polished to define a highly reflective surface adapted to reflect light which is directed proximally from the biologically material thereby to minimize absorption of the reflected light by the holder.

13. A catheter as defined in claim 1 further comprising:

said core having at least one radiopaque stripe extending longitudinally of the core.

14. A catheter as defined in claim 1 wherein at least the inner surface of the core which defines the lumen is a low friction material.

15. A catheter as defined in claim 1 further comprising:

a gasket interposed between the holder and the cap, the gasket having cut-out regions in alignment with the optical fibers so as to be out of the path of the beam emitted from the conductors.

16. A catheter for removing biological material by laser energy, the catheter having a proximal end and a distal end and comprising:

a unitary catheter core surrounded by a catheter sheath, said core and sheath defining a catheter wall;

means defining a lumen extending through the catheter core, the lumen being open at the distal end of the catheter;

means at the proximal end of the lumen for permitting fluid communication with the lumen and to permit a guide wire to be received within the lumen;

a plurality of flexible optical conductors extending longitudinally of the catheter and within the catheter wall;

a distal cap mounted on the distal end of the catheter and covering the distal end of the fibers, the distal cap having a distal surface defining an emission surface and providing an optical path from the distal end of the fibers to the emission surface;

an aperture formed through the distal cap in communication with the catheter lumen;

the flexibility of the catheter being varied along its length by means comprising:

the core being formed from a plurality of articulated segments connected end to end and flexible joints; and the outer sheath being thin and flexible and being unconnected to the core so as not to restrict flexure of the core.

17. A catheter as defined in claim 16 further comprising:

the spacing of the articulations varying along the length of the core thereby to vary the flexibility of the catheter, the catheter having greater flexibility in those regions where the articulations are more closely spaced.

18. A catheter as defined in claim 17 wherein the articulations at the distal end of the catheter are more closely spaced than at the proximal end.

19. A catheter as defined in claim 16 wherein the articulated segments are defined by a plurality of circumferentially formed notches, spaced longitudinally along the core, the circumferential notches defining smaller diameter connecting segments between the articulated segments.

20. A catheter as defined in claim 16 further comprising:

a plurality of flutes formed longitudinally along the outside of the core, the conductors being received in and extending along the flutes;

a flexible sheath surrounding the core to retain the conductors within the flutes;

said conductors, core and sheath being substantially unattached to each other thereby to enable the core, conductors and sheath to shift longitudinally with respect to each other thereby to permit their simultaneous bending but without any of said core, conductor or sheath restricting the bending of the others.

21. A catheter as defined in claim 20 further comprising:

said conductors being secured by a holder ring having a central aperture and a plurality of circumferentially spaced apertures in the ring, each of the circumferentially spaced apertures receiving the distal end of a conductor, said holder being secured to the cap.

22. A catheter as defined in claim 21 wherein the distal cap further comprises:

a cylindrical member having a proximal bore adapted to receive the holder ring and the distal end of the core;

the cap having a smaller aperture formed distally of and in communication with the proximal bore, the smaller aperture opening at the distal end of the cap;

the juncture of the bore aperture defining a shoulder;

the distal face of the holder being in engagement with the shoulder.

23. A catheter as defined in claim 21 further comprising:

a gasket interposed between the holder and the cap and having a plurality of cut-outs in alignment with the conductors.

24. A catheter as defined in claim 23 wherein the gasket is optically transparent.

25. A catheter as defined in claim 24 wherein the distal cap further comprises:

a cylindrical member having a proximal bore adapted to receive the holder ring and a distal end of the core;

a cap having a smaller aperture formed distally of and in communication with the proximal bore, the smaller aperture opening at the distal end of the cap;

the juncture of the bore and aperture defining a shoulder;

said gasket being interposed between said shoulder and the distal face of the holder.

26. A catheter for removing biological material by laser energy, the catheter having a proximal end and a distal end and comprising:
   means defining a lumen extending through the catheter, the lumen being open at the distal end of the catheter, said means including a catheter wall;
   means at the proximal end of the lumen for permitting fluid communication with the lumen and to permit a guide wire to be received within the lumen;
   a plurality of flexible optical conductors extending longitudinally of the catheter and within the catheter wall;
   a distal cap mounted on the distal end of the catheter and covering the distal end of the fibers, the distal cap having a distal surface defining an emission surface and providing an optical path from the distal end of the fibers to the emission surface;
   an aperture formed through the distal cap in communication with the catheter lumen;
   the flexible optical conductors being contained in circumferentially spaced relation within the catheter wall;
   the distal cap including an annular portion which terminates in the emission surface;
   means for holding the distal faces of the conductor in optically transmissive relation to the cap to direct light from the conductors through the annular portion of the cap, the conductors being constructed and arranged to emit light in a divergent beam whereby the light emitted from each of the circumferentially spaced fibers may overlap increasingly in a distal direction;
   the distance of the emission surface of the cap from the distal ends of the fibers being such that the distance between the emission surface of the cap and the image plane in which the overlapping beams have diverge to define a peripheral envelope which is at least as great in diameter as the outer diameter of the catheter, said distance between the emission face and said image plane being not substantially greater than the diameter of the catheter.

27. A catheter as defined in claim 26 wherein said distance is not more than about 1.5 millimeters.

28. A catheter as defined in any of claims 1–27 further comprising, in combination, said guide wire.

29. A catheter as defined in claim 28 further comprising:
   said catheter being of a length and being dimensioned for advancement to and into a patient's coronary arteries whereby said biological material may be removed from said coronary arteries.

30. A flexible catheter construction comprising:
   an elongate one-piece, flexible core having a lumen extending therethrough, the core being formed from a plurality of articulated segments, the articulated segments being defined by a plurality of circumferentially formed notches, spaced longitudinally along the core, the circumferential notches defining smaller diameter connecting segments between the articulated segments; and
   a flexible outer sheath surrounding the core.

31. A catheter as defined in claim 29 further comprising:
   the spacing of the articulations connecting the articulated segments being varied, thereby to vary the flexibility of the composite catheter along its length.

32. A catheter for delivering laser energy to biological material at a selected location internally of a patient comprising:
   an elongate catheter body adapted to be placed internally of the patient, the catheter body having proximal and distal ends;
   optical fiber means carried by the catheter body and being constructed and arranged to direct laser light from the proximal end to the distal end and to emit a beam of laser light at the distal end of the catheter; and
   means at the distal end of the catheter for reflecting light reflected or radiated from the biological material thereby to reduce absorption of energy by the distal end of the catheter.

33. A catheter as defined in claim 32 further comprising:
   the catheter having a fiber holder at the distal end, the fiber holder having a distal face, the distal end of the optical fiber means being attached to the fiber holder, wherein the reflecting means comprises the distal face of the holder and the distal end of the fiber being highly polished.

34. A catheter as defined in claim 33 further comprising:
   a transparent end cap mounted to the catheter over and covering the distal end of the holder and the optical fiber means;
   the proximal face of the end cap being coated with an antireflection coating.

35. A catheter as defined in claim 33 wherein the fiber holder is formed from a metal.

36. A catheter as defined in claim 33 further comprising:
   said end cap and holder having a central aperture formed therethrough
   a gasket between the distal face of the holder and the proximal face of the end cap, the gasket being formed from an optically transparent material and having an opening in registry with the lumen.

37. A catheter as defined in any of claims 15, 10, 11, 12, 23, 24, 25, wherein said gasket is formed from medical grade silicone rubber.

38. A catheter as defined in claim 37 further comprising:
   said catheter being of a length and being dimensioned for advancement to and into a patient's coronary arteries whereby said biological material may be removed from said coronary arteries.

39. A catheter as defined in any of claims 1–27 or 30–36 further comprising said catheter being of a length and being dimensioned for advancement to and into a patient's coronary arteries whereby said biological material may be removed from said coronary arteries.

* * * * *